United States Patent [19]

Ort et al.

[11] Patent Number: 5,318,947

[45] Date of Patent: Jun. 7, 1994

[54] METHOD FOR CONTROLLING HARMFUL PLANTS IN RICE WITH 2-BENZOYL-1,3-CYCLOHEXANEDIONE DERIVATIVES

[75] Inventors: Oswald Ort, Kelkheim; Lothar Willms, Hillscheid; Hans-Joachim Zeiss, Sulzbach; Klaus Bauer, Hanau; Hermann Bieringer, Eppstein/Taunus, all of Fed. Rep. of Germany

[73] Assignee: Hoechst Aktiengesellschaft, Frankfurm am Main, Fed. Rep. of Germany

[21] Appl. No.: 856,170

[22] PCT Filed: Oct. 12, 1990

[86] PCT No.: PCT/EP90/01721

§ 371 Date: Jun. 9, 1992

§ 102(e) Date: Jun. 9, 1992

[87] PCT Pub. No.: WO91/05470

PCT Pub. Date: May 2, 1991

[30] Foreign Application Priority Data

Oct. 18, 1989 [DE] Fed. Rep. of Germany ....... 3934706
Nov. 25, 1989 [DE] Fed. Rep. of Germany ....... 3939094
Dec. 30, 1989 [DE] Fed. Rep. of Germany ....... 3943397

[51] Int. Cl.$^5$ .................... A01N 37/34; A01N 37/22; A01N 35/06
[52] U.S. Cl. .................... 504/310; 504/341; 504/348
[58] Field of Search .............. 504/348, 310, 341; A01N 35/06, 37/22, 37/34

[56] References Cited

U.S. PATENT DOCUMENTS 4,780,127 10/1988 Michaely et al. ............... 71/103
5,114,461 5/1992 Geach et al. ................... 71/88

FOREIGN PATENT DOCUMENTS 0137963 4/1985 European Pat. Off. .
0186118 7/1986 European Pat. Off. .
0274634 7/1988 European Pat. Off. .

Primary Examiner—Richard L. Raymond
Assistant Examiner—S. Mark Clardy
Attorney, Agent, or Firm—Curtis, Morris & Safford

[57] ABSTRACT

Compounds of the formula I

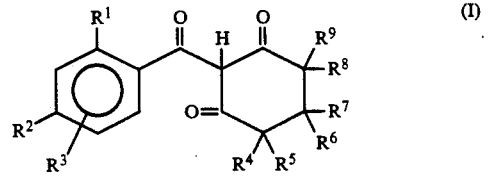

where $R^1$ to $R^9$ are as defined in claim 1 are known as herbicides. When these compounds are applied in traditionally used amounts, this often results in damage to crop plants in the crops, when it is desired to achieve sufficient action against weeds typically occurring therein. However, according to the invention it is possible to reduce the application rates to 0.001 to 0.5 kg of a.i./ha in rice growing, and the action obtained against important harmful plants in rice from the species Sagittaria, Cyperus and Scirpus Eleocharis is nevertheless sufficient.

17 Claims, No Drawings

METHOD FOR CONTROLLING HARMFUL PLANTS IN RICE WITH 2-BENZOYL-1,3-CYCLOHEXANEDIONE DERIVATIVES

The invention is in the field of the plant protection agents which can be employed against monocotyledon and dicotyledon weeds.

EP-A 0,137,963, EP-A 0,186,118, EP-A 0,274,634, EP-A 0,298,680 and US-A 4,780,127 disclose 2-benzoyl-cyclohexanedione derivatives which are described as agents for controlling a broad range of monocotyledon and dicotyledon weeds.

However, the application rates of from 0.56 to 4.48 kg of a.i./ha which were used in the tests known to date cause considerable damage to crop plants when the herbicides are employed against harmful plants in crops. If, in contrast, the application rate is lowered to such an extent that there is no, or only slight, damage to the crop plants, the result is an insufficient herbicidal action in many important crops against the harmful plants typically occurring therein, so that, in some cases, only synergistic mixtures permit the 2-benzoylcyclohexanedione derivatives to be employed sensibly (cf. EP-A-0,284,634).

It has now been found that the abovementioned compounds have an excellent selectivity in rice, the surprising fact being that an outstanding action against the harmful plants which typically occur in rice growing is retained, even when the dosages of active substance are low. In particular, perennial weeds which occur in rice growing and which are often difficult to control, for example Sagittaria spec., Cyperus serotimus, Scirpus maritimus, Eleocharis spec. and Scirpus juncoides, and a broad range of annual weeds, are controlled effectively.

The present invention therefore relates to a method for controlling harmful plants in rice growing, in which one or more compounds of the formula (I) or salts thereof

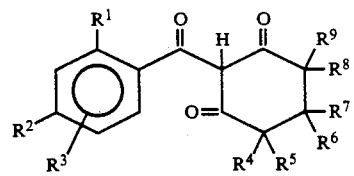
(I)

where $R^1$ is halogen, $(C_1-C_4)$ alkoxy, $(C_1-C_4)$ alkyl, $(C_1-C_4)$ haloalkyl, $-NO_2$, $-CN$ or $S(O)_nR^{10}$;

$R^2$ and $R^3$ independently of one another are hydrogen, halogen, $(C_1-C_4)$ alkyl, $(C_1-C_4)$ alkoxy, $OCF_3$, $(C_1-C_4)$-haloalkyl, $-CN$, $-NO_2$, $-S(O)_m-R^{11}$, $-NR^{12}R^{13}$, $-NR^{14}-CO-R^{15}$, $-CO-R^{16}$;

$R^4$, $R^6$, $R^7$, $R^8$ and $R^9$ independently of one another are hydrogen or $(C_1-C_4)$ alkyl;

$R^5$ is hydrogen, $(C_1-C_4)$ alkyl or $-CO-O-(C_1-C_4)$ alkyl;

$R^{10}$ is $(C_1-C_4)$ alkyl, $(C_1-C_4)$ haloalkyl or $(C_1-C_4)$ alkoxy;

$R^{11}$ is $(C_1-C_4)$ alkyl, $(C_1-C_4)$ haloalkyl, phenyl, benzyl or $-NR^{17}R^{18}$;

$R^{12}$ and $R^{13}$ independently of one another are hydrogen or $(C_1-C_4)$ alkyl;

$R^{14}$ is hydrogen or $(C_1-C_4)$ alkyl;

$R^{15}$ is $(C_1-C_4)$ alkyl;

$R^{16}$ is hydrogen, $(C_1-C_4)$ alkyl, $(C_1-C_4)$ haloalkyl or $(C_1-C_4)$ alkoxy;

$R^{17}$ and $R^{18}$ independently of one another are hydrogen or $(C_1-C_4)$ alkyl and n and m independently of one another are 0, 1 or 2, are applied to the area under cultivation which contains harmful plants and rice plants or their seeds, in an effective amount of from 0.001 to 0.5 kg of a.i./ha, preferably 0.01 to 0.2 kg of a.i./ha, in particular 0.02 to 0.12 kg of a.i./ha.

The method according to the invention is of particular interest with compounds of the abovementioned formula (I) or their salts where $R^1$ is fluorine, chlorine, bromine, iodine, methoxy, nitro, cyano or $-S(O)_nR^{10}$;

$R^2$ and $R^3$ independently of one another are hydrogen fluorine, chlorine, bromine, iodine, methyl, methoxy trifluoromethoxy, cyano, nitro, trifluoromethyl $-SO_2R^{11}$, $-NR^{12}R^{13}$, $-N(CH_3)-CO-R^{15}$ or $-CO-O-(C_1-C_4)$ alkyl and $R^4$, $R^5$, $R^6$, $R^7$, $R^8$ and $R^9$ independently of one another are hydrogen or methyl, and $R^{10}$, $R^{11}$, $R^{12}$, $R^{13}$, $R^{14}$ and n are as defined above.

The method according to the invention is particularly preferred with compounds of the formula (I) or their salts, in which $R^2$ and $R^3$ independently of one another are hydrogen, fluorine, chlorine, bromine, $-N(CH_3)_2$, methoxy, nitro, $-SO_2CH_3$, $-SO_2C_2H_5$, $-SO_2CH_2Cl$, $-SO_2N(CH_3)_2$ or trifluoromethyl and n is 2, and $R^1$, $R^4$, $R^5$, $R^6$, $R^7$, $R^8$ and $R^9$ are as defined above.

The compounds of the formula (I) can be present in various tautomeric structures (keto/enol tautomery) and have a very acidic hydrogen atom on the methine group between the three carbonyl groups, which hydrogen atom can be replaced by a cation suitable for agriculture. The salts which are then present are generally metal salts, in particular alkali metal salts, alkaline earth metal salts, optionally substituted or unsubstituted ammonium, sulfonium or phosphonium salts in which the substituents can be aliphatic or aromatic radicals. Suitable bases for preparing the salts according to the invention are, for example, alkali metal carbonates such as potassium carbonate, alkali metal hydroxides and alkaline earth metal hydroxides, ammonia or ethanolamine.

Alkyl radicals are understood as meaning radicals having the stated number of carbon atoms. The radicals can be straight-chain or branched. The most common radicals are, for example, methyl, ethyl, n-propyl, isopropyl, n-butyl, isobutyl, sec.-butyl to tert.-butyl. Halogen is understood as meaning fluorine, chlorine, bromine or iodine. Haloalkyl radicals can be monosubstituted or polysubstituted by halogen, i.e. they can also be perhalogenated.

Particularly suitable compounds of the formula (I) in the herbicidal agents to be employed according to the invention are, for example, 2-(2-chloro-4-methylsulfonylbenzoyl)-1,3-cyclohexanedione (Ia) (see Example 1, chemical examples), 2-(2-nitrobenzoyl)-4,4-dimethyl-1,3-cyclohexanedione (Ib) (see Table 1, Example 12), 2-(2-chloro-4-ethylsulfonylbenzoyl)-5,5-dimethyl-1,3-cyclo-hexanedione (Ic, Table 1, Example 5), 2-(2-nitro-4-chlorobenzoyl)-4-(1-methylethyl)-1,3-cyclohexanedione (Id, Table 1, Example 38), 2-(2-nitro-4-chlorobenzoyl)-4,4-dimethyl-1,3-cyclohexanedione (Ie, Table 1, Example 7), 2-(2-chloro-4-methylsulfonylbenzoyl)-4,4- dimethyl-6-methyl-1,3-cyclohexanedione (If, Table 1, Example 18). The 2-benzoylcyclohexanedione derivatives of the formula (I) have been disclosed, see, for example, the above-mentioned EP-A Publications No. 0,137,963, 0,186,118, 0,274,634 and 0,298,680 and U.S. Pat. No. 4,780,127, or they can be prepared by the methods stated in these publications.

The herbicidal agents employed according to the invention have an excellent herbicidal activity against a broad range of economically important monocotyledon and dicotyledon harmful plants in rice growing. The active substances also act efficiently on perennial weeds which produce shoots from rhizomes, rootstocks or other perennial organs and which are difficult to control. In this context, it does not matter whether the substances are applied before sowing, pre-emergence or post-emergence. Pre-emergence and/or early post-emergence application is preferred. representatives of the monocotyledon and dicotyledon weed flora which can be controlled by the agents according to the invention, without the enumeration being a restriction to certain species.

Examples of weed species on which the active substance combinations act efficiently are, from amongst the monocotyledons, Cyperus species from the annual sector and from amongst the perennial species perennial Cyperus species, Scirpus species and also Eleocharis species.

Weeds which occur under the specific conditions of rice growing such as, for example, Sagittaria, Alisma, Eleocharis, Scirpus, Cyperus etc. are controlled outstandingly by the active substances to be employed according to the invention.

In dicotyledon weed species, the spectrum of action extends to, for example, Rotala, Sphenoclea, Eclipta, Potamogeton, Heteranthera, Aeschynomene and Ammannia.

If the compounds employed according to the invention are applied to the soil surface before germination, the weeds grow until they have reached the cotyledon stage, but then growth stops, and, eventually, they die completely after three to four weeks have elapsed.

When the compounds of the formula (I) or their salts are applied post-emergence to the green parts of the plants, growth likewise stops drastically a very short time after the treatment, and the weed plants remain at the growth stage of the time of application, or they die after a certain time, so that, in this manner, competition by the weeds, which is harmful to the crop plants, can be eliminated at a very early point in time and in a sustained manner by applying the compounds of the formula (I) according to the invention or their salts.

Even though the compounds employed according to the invention have an outstanding herbicidal activity against monocotyledon and dicotyledon weeds, rice crops of sown or transplanted rice are not damaged, or only to a negligible extent. The compounds of the formula (I) or their salts are therefore highly suitable for selectively controlling harmful plants in rice crops.

The application rate of the compounds of the formula (I) or their salts depend on the circumstances as regards weather and soil, as well as on the specific harmful plants and on the rice varieties, and they are generally in the range of from 0,001 to 0.5 kg of a.i./ha, preferably 0.01 to 0.2 kg of a.i./ha. A late pre-emergence or early post-emergence application with 0.02 to 0.12 kg of a.i./ha is particularly preferred.

The compounds of the formula (I) or their salts can be formulated in different ways, depending on the prevailing biological and/or chemico-physical parameters. The following are suitable as possible formulations: wettable powders (WP), water-soluble powders (SP), emulsifiable concentrates (EC), aqueous solutions or concentrates (SL), emulsions (EW) such as oil-in-water and water-in-oil emulsions, sprayable solutions, capsule suspensions (CS), dispersions on an oil or water base, suspoemulsions, suspension concentrates (SC), dusting powders (DP), solutions which can be mixed with oils (OL), seeddressing agents, granules (GR) in the form of microgranules, spray granules, coated granules and adsorption granules, granules for soil application or broadcasting, water-dispersible granules (WG), ULV formulations, microcapsules and waxes.

These individual types of formulations are known in principle and are described, for example, in: Winnacker-Kuchler, "Chemische Technologie [Chemical Technology]", Volume 7, C. Hauser Verlag Munich, 4th Ed. 1986; van Valkenburg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives are likewise known and are described, for example, in: Watkins, "Handbook of Insecticide Dust Diluents and Carriers", 2nd Ed., Darland Books, Caldwell N.J.; H.v. Olphen, "Introduction to Clay Colloid Chemistry"; 2nd Ed., J. Wiley & Sons, N.Y., Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte [Surface-active Ethylene Oxide Adducts]", Wiss. Verlagsgesell., Stuttgart 1976; and Winnacker-Küchler, "Chemische Technologie [Chemical Technology]", Volume 7, C. Hauser Verlag Munich, 4th Ed. 1986.

Combinations with other pesticidally active substances such as other herbicides, fungicides or insecticides, as well as fertilizers and/or growth regulators, can also be prepared on the basis of these formulations, for example in the form of a readymix or as a tank mix.

Wettable powders are preparations which are uniformly dispersible in water and which, besides the active substance, also contain wetting agents, for example polyoxethylated alkylphenols, polyoxalkylated fatty alcohols or polyoxalkylated fatty amines, alkane- or alkylbenzenesulfonates, and dispersing agents, for example sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance.

Emulsifiable concentrates are prepared by dissolving the active substance in an organic solvent, for example butanol, cyclohexanone, dimethyiformamide, xylene and also higher-boiling aromatic compounds or hydrocarbons, with the addition of one or more emulsifiers. Examples of emulsifiers which can be used are: calcium salts of an alkylarylsulfonic acid, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting powders can be obtained by grinding the active substance with finely divided solid substances, for example talc or natural clays, such as kaolin, bentonite, pyrophillite or diatomaceous earth.

Granules can be produced either by spraying the active substance onto adsorptive, granulated inert material or by applying active substance concentrates onto the surface of carriers, such as sand, kaolinites or of granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

As a rule, the agrochemical preparations contain 0.1 to 99 percent by weight, in particular 2 to 95% by weight, of active substances of the formula (I), it being possible for the ideal concentrations in the formulations to vary.

The concentration of active substance in wettable powders is, for example, about 10 to 95% by weight, the remainder to 100% by weight is composed of conventional formulation components. In the case of emulsifiable concentrates, the concentration of active substance can be about 1 to 85% by weight, preferably 5 to 80% by weight. Formulations in the form of dusts usually contain about 1 to 25% by weight, mostly 5 to 20% by weight of active substance, sprayable solutions about 0.2 to 25% by weight, preferably 2 to 20% by weight, of active substance. In the case of granules, such as water-dispersible granules, the active substance content depends partly on whether the active compound is liquid or solid and on which granulation auxiliaries and fillers are used. The content in water-dispersible granules is generally between 10 and 90% by weight.

In addition, the active substance formulations mentioned contain, if appropriate, the adhesives, wetting agents, dispersing agents, emulsifiers, penetrants, solvents, fillers or carriers which are conventional in each case.

For use, the formulations, present in commercially available form, are diluted, if appropriate, in a customary manner, for example using water in the case of wettable powders, emulsifiable concentrates, dispersions and water-dispersible granules. Preparations in the form of dusts, granules for soil application and/or broadcasting, and also sprayable solutions are usually not further diluted with other inert substances before use.

The application rate required for the compounds of the formula (I) varies with the external conditions, such as, inter alia, temperature, humidity, and the nature of the herbicide used.

The examples which follow serve to illustrate the invention:

A. Formulation Examples a) A dusting agent is obtained by mixing 10 parts by weight of an active substance of the formula (I) or a salt thereof and 90 parts by weight of talc as inert substance and comminuting the mixture in a hammer mill.

b) A wettable powder which is readily dispersible in water is obtained by mixing 25 parts by weight of active substance of the formula (I) or a salt thereof, 64 parts by weight of kaolin-containing quartz as the inert substance, 10 parts by weight of potassium ligninsulfonate and 1 part by weight of sodium oleoylmethyltaurinate as the wetting and dispersing agent, and grinding the mixture in a pinned-disk mill.

c) A dispersion concentrate which is readily dispersible in water is obtained by mixing 20 parts by weight of active substance of the formula (I) or a salt thereof with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255° to above 277° C.), and grinding the mixture in a ball mill to a fineness of below 5 microns.

d) An emulsifiable concentrate is obtained from 15 parts by weight of herbicidal active substance, 75 parts by weight of cyclohexanone as the solvent and 10 parts by weight of oxethylated nonylphenol as the emulsifier.

e) Water-dispersible granules are obtained by mixing 75 parts by weight of active substance of the
   formula (I) or a salt thereof,
10 parts by weight of calcium ligninsulfonate,
5 parts by weight of sodium lauryl sulfate,
3 parts by weight of polyvinyl alcohol and
7 parts by weight of kaolin, grinding the mixture on a pinned-disk mill, and granulating the powder in a fluidized bed by spraying on water as the granulation liquid.

f) Water-dispersible granules are also obtained by homogenizing on a colloid mill and comminuting 25 parts by weight of active substance of the
   formula (I) or a salt thereof,
5 parts by weight of sodium 2,2',-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water, subsequently grinding the mixture on a bead mill, and atomizing and drying the resulting suspension in a spray tower by means of a single-fluid nozzle.

B. Chemical examples

Example 1

2-[2-chloro-4- (methylsulfonyl) benzoyl]-1,3-cyclohexanedione 42.5 g of 2-chloro-4-methylsulfonylbenzoic acid were boiled in 160 ml of dioxane with 5 drops of dimethylformamide and 25.1 ml of thionyl chloride until the evolution of gas subsided. The solvent was stripped off with the exclusion of moisture on a rotary evaporator. To the oily residue there were added at 0° C. 19.7 g of 1,3-cyclohexanedione in 250 ml of acetonitrile, and 63.1 ml of triethylamine were then added dropwise at this temperature. Stirring was continued for 15 minutes, 15.3 ml of acetone cyanohydrin were added, and the mixture was allowed to stand overnight. The reaction mixture was concentrated under reduced pressure on a rotary evaporator, the residue was taken up in ethyl acetate/water, and the organic phase was washed with 2N hydrochloric acid. The product was extracted from the organic phase using 5% $K_2CO_3$ solution, and precipitated at a pH of 2-3 using concentrated hydrochloric acid, with cooling. After filtration with suction and drying, 48.4 g of 2-[2-chloro-4-(methylsulfonyl)benzoyl]-1,3-cyclohexanedione of melting point 141°–142° C. were obtained.

The compounds listed in Table 1 were obtained analogously:

TABLE 1

$$\text{(I)}$$

Structure: substituted benzoyl-cyclohexanedione with substituents $R^1, R^2, R^3$ on benzene ring and $R^4, R^5, R^6, R^7, R^8, R^9$ on cyclohexanedione ring.

| Example No. | $R^1$ | $R^2$ | $R^3$ | $R^4$ | $R^5$ | $R^6$ | $R^7$ | $R^8$ | $R^9$ | Melting point [°C.] |
|---|---|---|---|---|---|---|---|---|---|---|
| 2 | —NO$_2$ | —Cl | H | H | H | H | H | H | H | 183 |
| 3 | —NO$_2$ | —H | 2-CH$_3$ | H | H | CH$_3$ | CH$_3$ | H | H | 112 |
| 4 | —Cl | —SO$_2$C$_2$H$_5$ | H | H | H | H | H | H | H | Oil |
| 5 | —Cl | —SO$_2$C$_2$H$_5$ | H | H | H | CH$_3$ | CH$_3$ | H | H | Oil |
| 6 | —Cl | —NO$_2$ | H | CH$_3$ | CH$_3$ | H | H | H | H | 90 |
| 7 | —NO$_2$ | —Cl | H | CH$_3$ | CH$_3$ | H | H | H | H | 126 |
| 8 | —NO$_2$ | —Cl | H | H | H | CH$_3$ | CH$_3$ | H | H | 119 |
| 9 | —H | —H | 3-CF$_3$O | H | H | CH$_3$ | CH$_3$ | H | H | Oil |
| 10 | —Cl | —F | H | H | H | CH$_3$ | CH$_3$ | H | H | Oil |
| 11 | —Cl | —SO$_2$CH$_3$ | H | H | i-C$_3$H$_7$ | H | H | H | H | Oil |
| 12 | —NO$_2$ | —H | H | CH$_3$ | CH$_3$ | H | H | H | H | Oil |
| 13 | —NO$_2$ | —H | H | H | CH$_3$ | H | H | CH$_3$ | CH$_3$ | Oil |
| 14 | —NO$_2$ | —Cl | H | CH$_3$ | H | H | H | CH$_3$ | CH$_3$ | Oil |
| 15 | —Cl | —NO$_2$ | H | CH$_3$ | CH$_3$ | H | H | CH$_3$ | H | Oil |
| 16 | —Cl | —Cl | H | i-C$_3$H$_7$ | H | H | H | H | H | Oil |
| 17 | —Cl | —SO$_2$CH$_3$ | H | CH$_3$ | CH$_3$ | H | H | H | H | Oil |
| 18 | —Cl | —SO$_2$CH$_3$ | H | CH$_3$ | CH$_3$ | H | H | H | CH$_3$ | Oil |
| 19 | —NO$_2$ | —H | H | CH$_3$ | CH$_3$ | CH$_3$ | H | H | H | Oil |
| 20 | —NO$_2$ | —Cl | H | H | H | H | CH$_3$ | CH$_3$ | CH$_3$ | Oil |
| 21 | —Cl | —NO$_2$ | H | CH$_3$ | CH$_3$ | CH$_3$ | H | H | H | Oil |
| 22 | —Cl | —SO$_2$CH$_3$ | H | CH$_3$ | CH$_3$ | CH$_3$ | H | H | H | Oil |
| 23 | —NO$_2$ | —H | H | H | H | H | H | H | H | 142 |
| 24 | —H | —H | 3-NO$_2$ | H | H | H | H | H | H | 87 |
| 25 | —H | —H | 3-NO$_2$ | H | H | CH$_3$ | CH$_3$ | H | H | 82 |
| 26 | —F | —H | 6-F | H | H | H | H | H | H | 86 |
| 27 | —F | —H | 6-F | CH$_3$ | CH$_3$ | H | H | H | H | 95 |
| 28 | —F | —H | 6-F | H | H | CH$_3$ | CH$_3$ | H | H | Oil |
| 29 | —OCH$_2$ | —H | 6-OCH$_3$ | H | H | CH$_3$ | CH$_3$ | H | H | 153 |
| 30 | —NO$_2$ | —H | 5-Cl | H | H | H | H | H | H | 165 |
| 31 | —NO$_2$ | —H | 5-Cl | H | H | H | H | CH$_3$ | CH$_3$ | 122 |
| 32 | —NO$_2$ | —H | 5-Cl | H | H | CH$_3$ | CH$_3$ | H | H | 132 |
| 33 | —NO$_2$ | —H | 5-Cl | H | CH$_3$ | H | H | CH$_3$ | CH$_3$ | 119 |
| 34 | —Cl | —SO$_2$CH$_3$ | H | H | H | CH$_3$ | CH$_3$ | H | H | 138–139 |
| 35 | —NO$_2$ | —H | H | H | H | CH$_3$ | CH$_3$ | H | H | 132–134 |
| 36 | —Cl | —Cl | H | H | H | H | H | H | H | 102–104 |
| 37 | —Cl | —F | H | H | H | H | H | H | i-C$_3$H$_7$ | Oil |
| 38 | —NO$_2$ | —Cl | H | H | H | H | H | i-C$_3$H$_7$ | H | 108 |

C. Biological examples

1. Pre-emergence action against weeds and selectivity

Weeds which occur in rice growing and rice plants are grown in waterlogged soil, for which purpose the pots are filled with sufficient water to reach the soil surface or flood it by up to a few millimeters.

The active substances of the formula (I) or the salts thereof which are formulated in the form of wettable powders or emulsion concentrates are then applied as aqueous suspensions or emulsions at an application rate of 600 to 800 l of water/ha (converted), in various dosages.

After the treatment, the pots are placed in a greenhouse and kept under good growth conditions for the test plants. After the test plants had emerged, the damage to the plants, or the negative effects on the emergence, was scored visually after a test period of 3 to 4 weeks by comparison with untreated controls.

The damage of the weed plants or the tolerance by crop plants was scored using a key in which the effectiveness is expressed by figures of scores of from 0 to 5. The figures denote:

0 = without action
1 = 0 to 20% action or damage
2 = 20 to 40% action or damage
3 = 40 to 60% action or damage
4 = 60 to 80% action or damage
5 = 80 to 100% action or damage In some examples, the action is additionally given in percentages (see values in brackets).

The active substances employed according to the invention have a good herbicidal pre-emergence activity against a broad range of grass weeds and dicotyledon weeds, but impart little, or no, damage to the rice plants. Some results are compiled in Table 2.

TABLE 2

Pre-emergence action

| Active substance Example No. | Dose in kg/ha | Score (% damage) | | | | | | |
|---|---|---|---|---|---|---|---|---|
| | | OSV | OSS | SAPA | ELAC | CYMO | SCMA | SCJU |
| 1 | 0.06 | 0 (0) | 2 (25) | 5 (93) | 5 (95) | 5 (98) | 5 (99) | 5 (95) |
| | 0.03 | 0 (0) | 1 (20) | 5 (90) | 5 (90) | 5 (98) | 5 (97) | 4 (75) |
| | 0.015 | 0 (0) | 0 (0) | 4 (75) | 5 (85) | 5 (98) | 5 (88) | 4 (70) |
| | 0.008 | 0 (0) | 0 (0) | 3 (60) | 4 (80) | 5 (98) | 4 (75) | 3 (50) |
| 34 | 0.06 | 1 | 2 | 5 | 5 | 5 | 5 | 3 |
| | 0.03 | 0 | 1 | 5 | 5 | 5 | 5 | 2 |
| | 0.015 | 0 | 0 | 4 | 4 | 4 | 5 | 2 |
| | 0.008 | 0 | 0 | 3 | 4 | 3 | 2 | 2 |
| 36 | 0.12 | 0 | 0 | 4 | 4 | 5 | 1 | 0 |
| | 0.06 | 0 | 0 | 2 | 2 | 5 | 1 | 0 |
| | 0.03 | 0 | 0 | 1 | 1 | 4 | 0 | 0 |
| | 0.015 | 0 | 0 | 1 | 0 | 4 | 0 | 0 |
| 38 | 0.12 | 0 | 2 | 5 | 5 | 5 | — | — |
| 39 | 0.12 | 2 | 3 | 5 | 4 | 4 | — | — |
| | 0.06 | 1 | 3 | 4 | 4 | 4 | — | — |
| | 0.03 | 0 | 2 | 4 | 3 | 2 | — | — |
| 16 | 0.5 | 2 | 2 | 5 | 5 | 5 | — | — |
| | 0.25 | 1 | 1 | 5 | 5 | 5 | — | — |
| | 0.12 | 0 | 0 | 5 | 4 | 4 | — | — |
| | 0.06 | 0 | 0 | 5 | 2 | 4 | — | — |
| 6 | 0.5 | 2 | 3 | 5 | 5 | 5 | — | — |
| | 0.25 | 1 | 2 | 5 | 4 | 5 | — | — |
| | 0.12 | 1 | 1 | 5 | 4 | 4 | — | — |
| | 0.06 | 0 | 1 | 4 | 2 | 2 | — | — |
| 7 | 0.06 | 2 | 3 | 5 | 5 | 5 | — | — |
| | 0.03 | 1 | 1 | 5 | 5 | 5 | — | — |
| 18 | 0.06 | 1 | 3 | 5 | 5 | 5 | — | — |
| | 0.03 | 0 | 1 | 5 | 5 | 5 | — | — |
| 5 | 0.12 | 1 | 3 | 5 | 5 | 5 | — | — |
| | 0.06 | 0 | 3 | 5 | 5 | 5 | — | — |
| 11 | 0.12 | 1 | 5 | 5 | 5 | 5 | — | — |
| | 0.06 | 0 | 3 | 5 | 4 | 4 | — | — |
| 12 | 0.06 | 1 | 3 | 5 | 5 | 3 | — | — |
| | 0.03 | 0 | 1 | 4 | 4 | 3 | — | — |
| 13 | 0.25 | 1 | 3 | 5 | 5 | 5 | — | — |
| | 0.12 | 1 | 1 | 5 | 5 | 5 | — | — |
| | 0.06 | 0 | 1 | 5 | 4 | 5 | — | — |
| | 0.03 | 0 | 0 | 3 | 3 | 3 | — | — |
| 15 | 0.5 | 2 | 3 | 5 | 5 | 5 | — | — |
| | 0.25 | 0 | 1 | 5 | 5 | 5 | — | — |
| | 0.12 | 0 | 0 | 5 | 5 | 5 | — | — |
| | 0.06 | 0 | 0 | 4 | 5 | 4 | — | — |
| 4 | 0.25 | 1 | 3 | 5 | 5 | 5 | — | — |
| | 0.12 | 0 | 2 | 5 | 5 | 5 | — | — |
| | 0.06 | 0 | 1 | 5 | 4 | 5 | — | — |
| | 0.03 | 0 | 1 | 4 | 3 | 5 | — | — |
| 19 | 0.12 | 2 | 3 | 5 | 5 | 5 | — | — |
| | 0.06 | 0 | 2 | 5 | 5 | 5 | — | — |
| | 0.03 | 0 | 1 | 4 | 4 | 4 | — | — |
| 20 | 0.06 | 2 | 4 | 5 | 5 | 5 | — | — |
| | 0.03 | 1 | 2 | 5 | 5 | 5 | — | — |
| 21 | 0.25 | 1 | 1 | 5 | 5 | 5 | — | — |
| | 0.12 | 0 | 1 | 5 | 5 | 5 | — | — |
| | 0.06 | 0 | 0 | 3 | 4 | 5 | — | — |
| | 0.03 | 0 | 0 | 2 | 3 | 3 | — | — |
| 2 | 0.25 | 0 | 3 | 5 | 5 | 5 | — | — |
| | 0.12 | 0 | 2 | 5 | 5 | 5 | — | — |
| | 0.06 | 0 | 2 | 5 | 5 | 5 | — | — |
| | 0.03 | 0 | 1 | 5 | 5 | 5 | — | — |
| 23 | 0.5 | 1 | 2 | 5 | 5 | 5 | — | — |
| | 0.25 | 0 | 1 | 5 | 5 | 5 | — | — |
| | 0.12 | 0 | 0 | 5 | 5 | 5 | — | — |
| | 0.06 | 0 | 0 | 3 | 4 | 5 | — | — |
| 33 | 0.5 | 1 | 0 | 5 | 5 | 5 | — | — |
| | 0.25 | 0 | 0 | 5 | 5 | 5 | — | — |
| | 0.12 | 0 | 0 | 4 | 4 | 2 | — | — |
| | 0.06 | 0 | 0 | 2 | 4 | 1 | — | — |
| 31 | 0.5 | 1 | 1 | 4 | 5 | 4 | — | — |
| | 0.25 | 0 | 0 | 4 | 4 | 3 | — | — |
| | 0.12 | 0 | 0 | 3 | 3 | 1 | — | — |
| | 0.06 | 0 | 0 | 3 | 2 | 1 | — | — |
| 30 | 0.5 | 0 | 1 | 5 | 5 | 4 | — | — |
| | 0.25 | 0 | 0 | 5 | 4 | 4 | — | — |
| | 0.12 | 0 | 0 | 5 | 2 | 4 | — | — |

TABLE 2-continued

|  |  | Pre-emergence action | | | | | | |
|---|---|---|---|---|---|---|---|---|
| Active substance Example No. | Dose in kg/ha | Score (% damage) | | | | | | |
|  |  | OSV | OSS | SAPA | ELAC | CYMO | SCMA | SCJU |
|  | 0.06 | 0 | 0 | 3 | 1 | — | — | — |

Abbreviations:
OSV *Oryza sativa*, transplanted-rice
OSS *Oryza sativa*, sown-rice
SAPY *Sagittaria pygmea*
ELAC *Eleocharis acicularis*
CYMO *Cyperus montis*
SCMA *Scirpus maritimus*-common sea club-rush
SCJU *Scirpus juncoides*-rush
Dose = Dose based on pure active substance [= kg of a.i./ha where a.i. = active ingredient]

2. Post-emergence action on weeds

Weeds which occur in rice growing and rice plants are grown in pots in which water covers the soil surface by up to 2 cm, and grown during the test phase. The test plants are treated in the three-leaf stage three weeks after sowing.

The active substances of the formula (I) or salts thereof which are formulated as wettable powders or emulsion concentrates are sprayed in various dosages on the green parts of the plants at an application rate of 300 to 600 l of water/ha (converted) and, after the test plants have remained in the greenhouse for about 3 to 4 weeks under ideal growth conditions, the effect of the preparations is scored visually by comparison with untreated controls. Alternatively, the active substances are also added directly to the irrigation water (application analogously to the so-called granule treatment) or sprayed onto plants and into the irrigation water. The agents according to the invention also have a good herbicidal post-emergence effectiveness against a broad range of economically important grass weeds and dicotyledon weeds, the damage to the rice plants being little or none at all (cf. Table 3).

TABLE 3

| Active substance Example No. | Dose in kg/ha | Post-emergence action: | | | | | | |
|---|---|---|---|---|---|---|---|---|
|  |  | OSV | OSS | SAPA | ELAC | CYMO | SCMA | SCJU |
| 1 | 0.12 | 2 (25) | 1 (8) | 5 (85) | 3 (60) | 5 (85) | 5 (95) | 5 (95) |
|  | 0.06 | 1 (15) | 0 (0) | 4 (75) | 3 (60) | 5 (85) | 5 (90) | 5 (93) |
|  | 0.03 | 0 (0) | 0 (0) | 4 (75) | 3 (60) | 4 (80) | 5 (83) | 5 (90) |
|  | 0.015 | 0 (0) | 0 (0) | 4 (75) | 4 (60) | 4 (80) | 4 (75) | 4 (80) |
| 34 | 0.12 | 4 | 1 | 3 | 5 | 5 | 5 | 4 |
|  | 0.06 | 2 | 0 | 2 | 5 | 5 | 4 | 3 |
|  | 0.03 | 1 | 0 | 2 | 4 | 5 | 4 | 2 |
|  | 0.15 | 0 | 0 | 1 | 4 | 5 | 4 | 2 |
| 36 | 0.5 | 1 | 1 | 5 | 4 | 5 | 2 | 1 |
|  | 0.25 | 1 | 0 | 5 | 4 | 4 | 1 | 0 |
|  | 0.12 | 0 | 0 | 4 | 3 | 3 | 0 | 0 |
| 38 | 0.5 | 3 | 0 | 3 | 4 | 5 | — | — |
|  | 0.25 | 2 | 0 | 2 | 4 | 4 | — | — |
| 39 | 0.25 | 2 | 4 | 5 | 4 | 5 | — | — |
|  | 0.12 | 2 | 3 | 5 | 4 | 4 | — | — |
| 16 | 0.5 | 1 | 0 | 2 | 4 | 5 | — | — |
|  | 0.25 | 0 | 0 | 2 | 4 | 4 | — | — |
| 6 | 0.5 | 0 | 0 | 3 | 3 | 5 | — | — |
| 15 | 0.5 | 1 | 0 | 4 | 5 | 5 | — | — |
|  | 0.25 | 0 | 0 | 3 | 5 | 5 | — | — |
|  | 0.12 | 0 | 0 | 2 | 4 | 4 | — | — |
| 4 | 0.25 | 1 | 0 | 4 | 4 | 5 | — | — |
|  | 0.12 | 0 | 0 | 3 | 3 | 5 | — | — |
| 19 | 0.25 | 0 | 0 | 2 | 4 | 5 | — | — |
| 2 | 0.25 | 0 | 0 | 3 | 5 | 5 | — | — |
|  | 0.12 | 0 | 0 | 2 | 4 | 5 | — | — |
|  | 0.06 | 0 | 0 | 2 | 4 | 5 | — | — |
|  | 0.03 | 0 | 0 | 2 | 4 | 5 | — | — |
| 23 | 0.5 | 0 | 0 | 3 | 4 | 4 | — | — |
|  | 0.25 | 0 | 0 | 2 | 3 | 4 | — | — |
|  | 0.12 | 0 | 0 | 2 | 3 | 3 | — | — |

Abbreviations: See Table 1

We claim:

1. A method for controlling harmful plants in rice growing, which comprises applying, to the area under cultivation which contains harmful plants and rice plants or their seeds, one or more compounds of the formula (I) or salts thereof

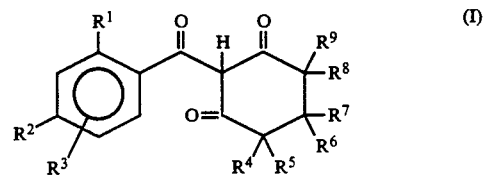

(I)

where
$R^1$ is halogen, ($C_1$-$C_4$) alkoxy, ($C_1$-$C_4$)alkyl, ($C_1$-$C_4$)haloalkyl, —$NO_2$, —CN or $S(O)_n R^{10}$;

$R^2$ and $R^3$ independently of one another are hydrogen, halogen, $(C_1-C_4)$alkyl, $(C_1-C_4)$alkoxy, $OCF_3$, $(C_1-C_4)$haloalkyl, $-CN$, $-NO_2$, $-S(O)_m-R^{11}$, $-NR^{12}R^{13}$, $-NR^{14}-CO-R^{15}$, $-CO-R^{16}$;

$R^4$, $R^6$, $R^7$, $R^8$ and $R^9$ independently of one another are hydrogen or $(C_1-C_4)$alkyl;

$R^5$ is hydrogen, $(C_1-C_4)$alkyl or $-CO-O-(C_1-C_4)$alkyl;

$R^{10}$ is $(C_1-C_4)$alkyl, $(C_1-C_4)$haloalkyl or $(C_1-C_4)$alkoxy;

$R^{11}$ is $(C_1-C_4)$alkyl, $(C_1-C_4)$haloalkyl, phenyl, benzyl or $-NR^{17}R^{18}$;

$R^{12}$ and $R^{13}$ independently of one another are hydrogen or $(C_1-C_4)$alkyl;

$R^{14}$ is hydrogen or $(C_1-C_4)$alkyl;

$R^{15}$ is $(C_1-C_4)$alkyl;

$R^{16}$ is hydrogen, $(C_1-C_4)$alkyl, $(C_1-C_4)$haloalkyl or $(C_1-C_4)$alkoxy;

$R^{17}$ and $R^{18}$ independently of one another are hydrogen or $(C_1-C_4)$alkyl and n and m independently of one another are 0, 1 and 2, in an effective amount of from 0.001 to 0.5 kg of a.i./ha.

2. The method as claimed in claim 1 wherein 0.01 to 0.2 kg of a.i./ha.

3. The method as claimed in claim 1 wherein the active substance of formula (I) is applied pre-emergence or early postemergence.

4. The method as claimed in claim 1 wherein 2-[2-chloro-4-(methylsulfonyl)benzoyl]-1,3-cyclohexanedione or a salt thereof is employed as the compound of the formula (I).

5. A method as claimed in claim 1, wherein 2-[2-chloro-4-(methylsulfonyl)-benzoyl]-1,3-cyclohexandione or a salt thereof is employed as the active substance of the formula (I).

6. A method as claimed in claim 1, wherein 0.01 to 0.2 kg a.i./ha of 2-[2-chloro-4-(methylsulfonyl)-benzoyl]-1,3-cyclohexandione or a salt thereof are applied as the active substance of the formula (I).

7. The method as claimed in claim 1, wherein $R^1$ is fluorine, chlorine, bromine, iodine, methoxy, nitro, cyano or $-S(O)_nR^{10}$;

$R^2$ and $R^3$ independently of one another are hydrogen, fluorine, chlorine, bromine, iodine, methyl, methoxy, trifluoromethoxy, cyano, nitro, trifluoromethyl, $-SO_2R^{11}$, $-NR^{12}R^{13}$, $-N(CH_3)-CO-R^{15}$ or $-CO-O(C_1-C_4)$alkyl and $R^4$, $R^5$, $R^6$, $R^7$, $R^8$ and $R^9$ independently of one another are hydrogen or methyl, and $R^{10}$, $R^{11}$, $R^{12}$, $R^{13}$, $R^{14}$ and n are as defined in claim 1.

8. A method as claimed in claim 7, wherein 0.01 to 0.2 kg a.i./ha of active substance of the formula (I) are applied pre-emergence or early post-emergence.

9. A method as claimed in claim 8, wherein 0.02 to 0.12 kg a.i./ha of active substance of the formula (I) are applied pre-emergence or early post-emergence.

10. The method as claimed in claim 1, wherein $R^2$ and $R^3$ independently of one another are hydrogen, fluorine, chlorine, bromine, $-N(CH_3)_2$, methoxy, nitro, $-SO_2CH_3$, $-SO_2CH_2Cl$, $-SO_2-C_2H_5-$, $-SO_2N(CH_3)_2$ or trifluoromethyl and n is 2, and $R^1$, $R^4$, $R^5$, $R^6$, $R^7$, $R^8$ and $R^9$ are as defined in claim 1.

11. The method as claimed in claim 10, wherein the active substances of formula (I) is applied at a rate of 0.02 to 0.12 kg of a.i./ha.

12. A method as claimed in claim 10, wherein 0.02 to 0.12 kg a.i./ha of active substance of the formula (I) are applied pre-emergence or early post-emergence.

13. A method as claimed in claim 10, wherein 0.01 to 0.2 kg a.i./ha of active substance of the formula (I) are applied pre-emergence or early post-emergence.

14. A method as claimed in claim 13, wherein 0.02 to 0.12 kg a.i./ha of active substance of the formula (I) are applied pre-emergence or early post-emergence.

15. The method as claimed in claim 1 wherein 2-(2-nitro-4-(chlorobenzoyl)-1,3-cyclohexanedione or a salt thereof is employed as the active substance of the formula (I).

16. The method of claim 1 wherein 2-(2-chloro-4-nitrobenzoyl)-4,4-dimethyl-6-methyl-1,3-chclohexanedione or a salt thereof is employed as the active substance of formula (I).

17. The method of claim 1 wherein 2-(2-chloro-4-methylsulfonylbenzoyl)-5,5-dimethyl-1,3-cyclohexanedione or a salt thereof is employed as the active substance of formula (I).

* * * * *